United States Patent [19]

Nelson

[11] 4,106,438
[45] Aug. 15, 1978

[54] METHOD OF HANDLING DROSOPHILA

[76] Inventor: Roger K. Nelson, 415 Layman La., Bloomington, Minn. 55420

[21] Appl. No.: 720,119

[22] Filed: Sep. 3, 1976

[51] Int. Cl.² ............................................. A01K 29/00
[52] U.S. Cl. ........................................... 119/1; 43/139
[58] Field of Search ............... 119/1, 15; 43/127, 128, 43/139; 128/188, 276, 1 C, DIG. 5; 35/20; 15/400

[56] References Cited

U.S. PATENT DOCUMENTS

| | | | |
|---|---|---|---|
| 2,300,765 | 11/1942 | Barnhart | 43/139 |
| 3,320,629 | 5/1967 | Zaidan | 15/400 |
| 3,769,936 | 11/1973 | Swanson et al. | 119/1 |
| 3,874,335 | 4/1975 | Galasso | 119/1 |

Primary Examiner—Russell R. Kinsey
Assistant Examiner—G. Lee Skillington
Attorney, Agent, or Firm—Schroeder, Siegfried, Ryan, Vidas & Steffey

[57] ABSTRACT

An improved method and apparatus for handling Drosophila including a simplified nozzle adapter designed to cooperate with the porous cellular obstruction plug in the end of a culture container to permit the passage of carbon dioxide gas therethrough to anesthetize the flies therein. After transferring flies to the sorting chamber for completing a selection process, the fly specimens may be simply and readily transferred to other study containers or culture vials through a suction apparatus positioned in the neck or entrance of the container to receive them.

10 Claims, 10 Drawing Figures

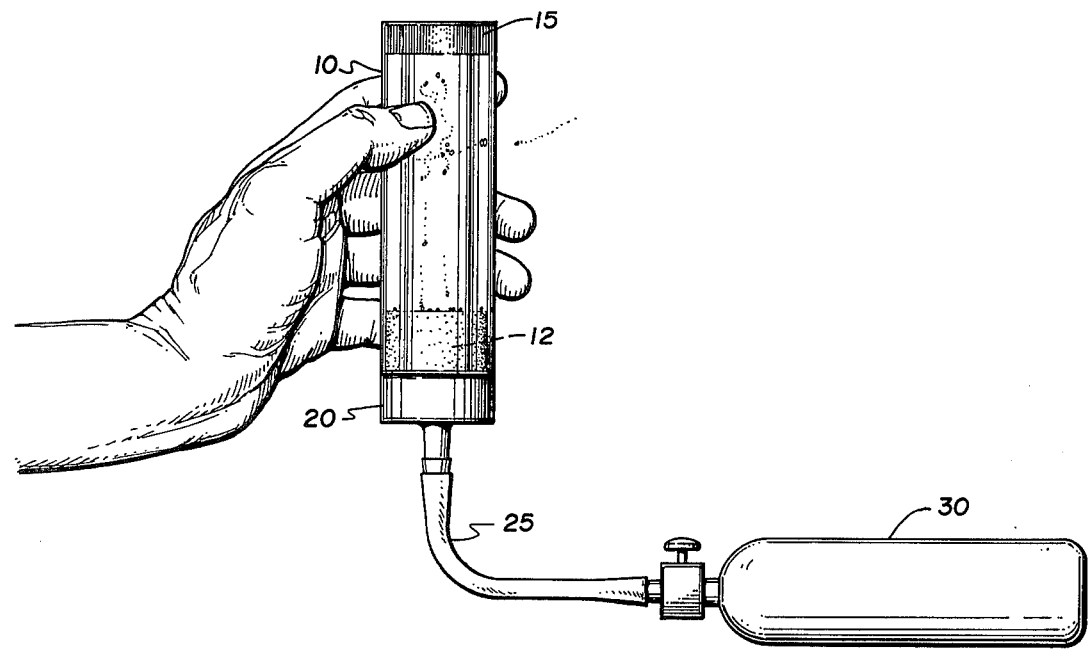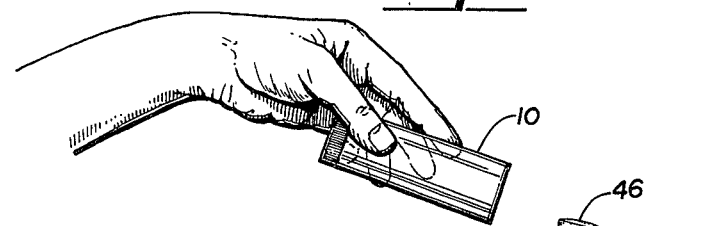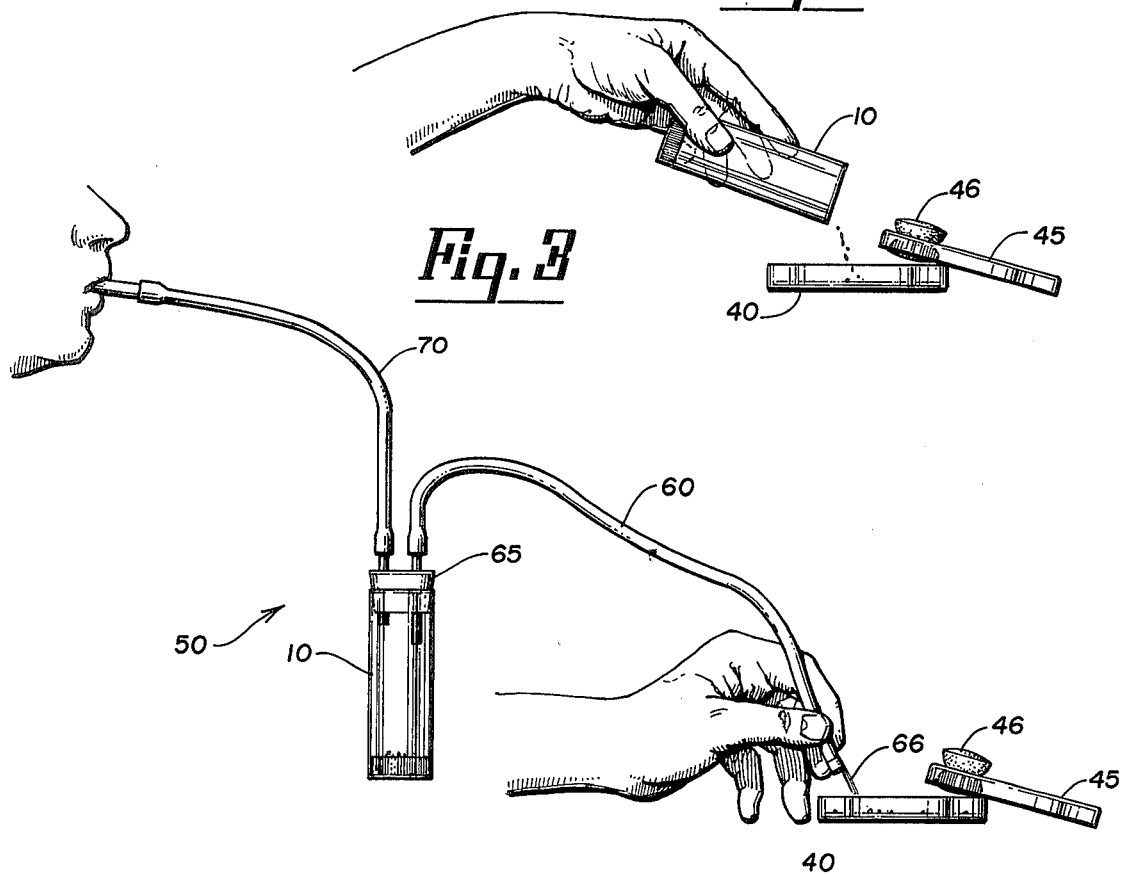

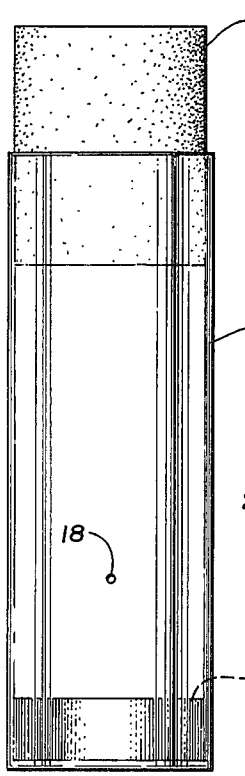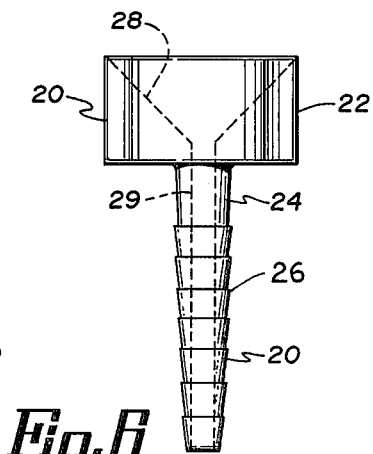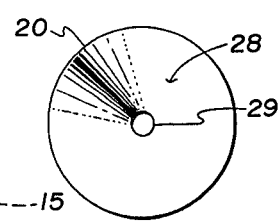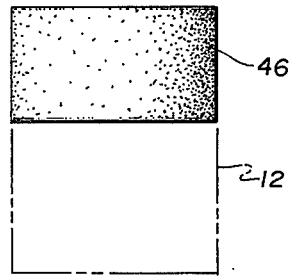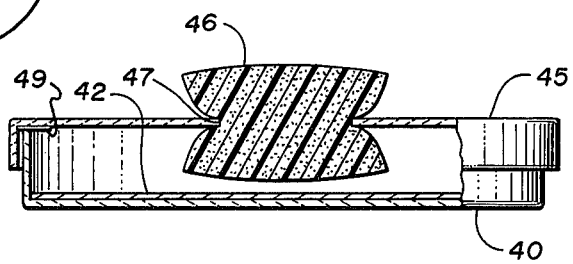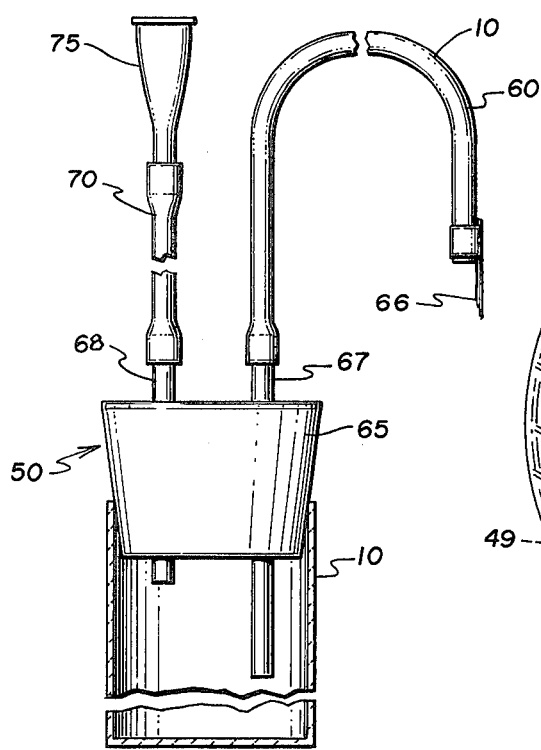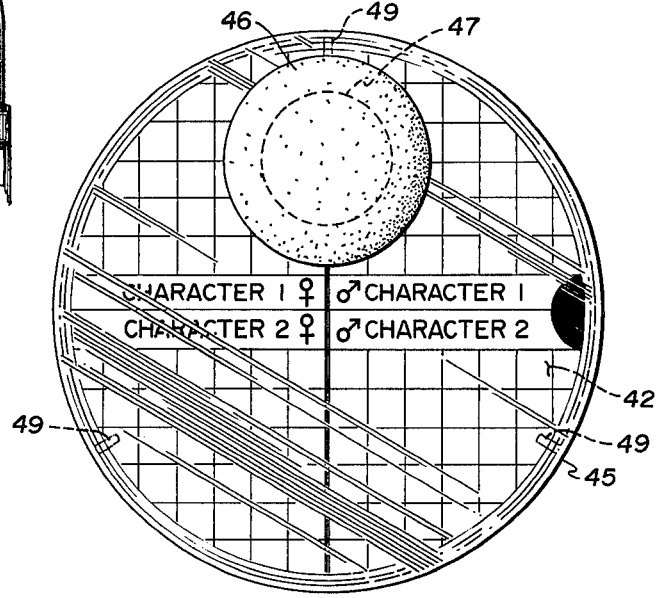

METHOD OF HANDLING DROSOPHILA

My invention relates to a method and appartus for handling Drosophila including means for anesthetizing, sorting, and transferring the Drosophila in the study of flies.

Equipment used in the study of Drosophila and research with the same is known and has taken a variety of forms. Generally, however, such equipment is so sophisticated to a point that students require supervision in the use of the same. This is particularly the case where ether is used as an anesthetizer for the Drosophila. Further, such equipment is not compatable with conventional apparatus used in culture studies.

The present invention is directed to an improved method of handling Drosophila from a breeding to a selection or separation and a rebreeding stage with simplified equipment which permits students to work unsupervised and which eliminates problems of ether explosion or escape of flies. The improved method and apparatus utilizes the technique of simply anesthetizing the flies with carbon dioxide, transferring the same to a conventional sorting and selection chamber, reanesthetizing them in the event that the flies become active before sorting is completed, and a simplied means for transferring selected species to new culture vials. The apparatus includes improvements in equipment which permits the use of commonly used culture containers and the introduction of carbon dioxide gas for the anesthetizing process, an improvement in the form of a cover for the sorting chamber so that the reanesthetizing may take place if needed, and a simplified means for transferring sorted flies through a vacuum system into a new culture container.

Therefore it is an object of this invention to provide an improved method and apparatus for handling Drosophila.

Another object of this invention is to provide simplified method and apparatus of this type which eliminates the need for supervision in the study of the fly or other insect.

A still further object of this invention is to provide improved apparatus which is readily adapted to conventional equipment, such as culture containers.

These and other objects of the invention will become apparent from the reading of the attached description together with the drawings wherein:

FIG. 1 is a schematic view of a step of anesthetizing the Drosophila in a culture container;

FIG. 2 is a schematic view of a step of transferring Drosophila from a culture container to a sorting container;

FIG. 3 is a schematic view of the steps of sorting of Drosophila in a sorting chamber and the transfer of selected species to a new culture chamber;

FIG. 4 is an elevation view of a conventional vial used as a culture container as modified for the new method and system, FIG. 5 is a side elevation view of a nozzle used in the anesthetizing of the Drosophila, FIG. 6 is a bottom elevation view of the nozzle of FIG. 5, FIG. 7 is a side elevation view of a conventional Petri dish used as a sorting chamber with the improved cover on the same, FIG. 8 is a top elevation view of the sorting chamber of FIG. 7, FIG. 9 is an elevation view of the porous plug used in the cover of the sorting chamber and in the vial of the culture chamber, and FIG. 10 is a schematic side elevation view of the transport mechanism for moving flies from the sorting chamber to a new culture chamber or vial for study.

FIG. 1 shows a conventional culture vial at 10 which may be used for breeding and growing of Drosophila or fly specimens for study purposes. Whenever it is desired to remove the specimens from the culture container, the vial, which has a porous plug 12 in the neck of the same, is inverted so that the foods section 15 adhering to the bottom of the vial will be inverted. A suitable nozzle adapter 20 is brought into contact with the porous plug 12 fitting over the end of the vial. The nozzle adapter is connected through a flexible tube or pipe 25 to a source of carbon dioxide shown as a bottle at 30, with a suitable control valve at the outlet of the same. Carbon dioxide is expelled through the nozzle adapter into the vial to anesthetize the flies therein. Normally a controlled pulse of a 3 second duration with a momentary pause of approximately 5 seconds and another 3 second pulse is sufficient to anesthetize all flies within the container. By inverting the vial, the anesthetized flies will be disposed adjacent to plug 12 instead of being disposed adjacent to the food source at the other extremity of the vial. When all flies are anesthetized and immobile, the porous plug 12 is removed and the flies, as indicated in FIG. 2, are dumped or poured into a sorting chamber shown at 40 in FIG. 2, the sorting chamber being of the type known as a Petri dish. The sorting chamber has a cover 45 with a plug 46 therein for purposes to be later noted. The immobile specimens in the sorting chamber may be then moved thereon for segregation purposes preparatory to removal of selected specimens from the sorting chamber. Should the specimens during the sorting process show signs of recovery before sorting and removal is completed, the cover 45 is positioned over the disc and an additional pulse of carbon dioxide gas from the adapter 20 will be directed into the sorting chamber through the porous plug 46 in the cover of the same.

Whenever sufficient sorting has been completed and it is desired to transfer specimens from the sorting chamber to a new culture chamber or vial for study of specimens, a simplified sorting and transferring apparatus 50 is used, as shown in FIG. 3. This transferring apparatus includes a flexible collecting tube 60 fitted through a stopper 65 in the end of a new vial or container with the opposite end of the collecting tube having a sorting brush 66 attached to or formed on the end of the same. A suitable suction pipe 70 also positioned through the stopper 65 permits the vacuum to be created in the vial or container 10 and through suction draws specimens from the selection chamber 40 into the new vial.

The apparatus involved in the system for handling Drosophila utilizes basically conventional components used in the study of fruit fly. Thus in FIG. 4, the vial 10 is a conventional one having the porous plug 12 positioned in one end of the same. The plug is an open cell sponge stopper which is compressed to form a barrier in the end of the vial. The vial will normally contain food in the base of the same such as is indicated in 15 in FIG. 1. A small vent passage 18 is drilled in the wall of the conventional vial so that as carbon dioxide gas is introduced through the porous plug in the anesthetizing of the fruit fly therein, air will be displaced through the vent passage 18 in the wall of the same. Such passage is of such diameter as to prevent egress of flies therefrom.

FIGS. 5 and 6 show the nozzle adapter 20 from the side and bottom. The nozzle adapter 20 is formed of any suitable material, either metal or plastic. It includes a hub section 22 and an adapter pipe 24 extending therefrom, with the adapter pipe having a series of conically shaped flanged sections 26 extending along the end of the same to permit connection of varying sized flexible tubing thereto for the purpose of directing the gas through the adapter. The opposite end of the adapter has a conically shaped recessed surface 28 communicating with the passage 29 through the adapter. As the adapter is brought into contact with the end of the culture vial 10 with the porous plug 12 therein, the edges of the porous plug are compressed and a flow passage for gas, such as carbon dioxide gas, is provided through the open cell structure of the stopper with the edge of the adapter at the recessed surface and the compressed portion of the porous plug forming a seal to prevent escape of gas except through the adapter into the interior of the vial.

FIGS. 7 and 8 show the sorting container the base of which is a conventional Petri dish with suitable indicia or a sectioned card 42 in the base of the same. The cover 45 has an internal diameter sufficient to fit loosely over the edges of the Petri dish and suitable raised hub portions 49 along the inner rim surface of the same rest on the upper peripheral edge of the Petri dish to space the cover slightly therefrom and provide a vent passage therebetween. This vent passage is a size sufficient to permit the escape of air from the Petri dish but normally will prevent the egress of flies therefrom. Cover 45 has a suitable aperture of 47 therein in which is positioned the porous plug 46. The porous plug 46 as shown in FIG. 9 is a cylindrical member of open cell sponge-like material similar to the porous plug 12 but of different height as indicated by the phantom lines. When the plug 46 is inserted into the aperture 47 which has a diameter smaller than the expanded external diameter of the cylindrical plug 46, the plug will be snugly fitted therein, as shown in FIG. 7. It will, however, permit passage of carbon dioxide therethrough. Thus whenever it is necessary to reanesthetize the flies being sorted, the cover 45 is placed over the dish and the adapter 20 is brought into contact with the plug 46 to compress the same and provide for the passage of the carbon dioxide gas therethrough into the sorting chamber to reanesthetize any flies which may have become mobile before the sorting process is completed. The plug 12 and 46 may be of varying sizes, as shown in FIG. 9, to fit varying sized openings in the vials and covers.

The transport mechanism 50, as shown in FIG. 10, includes a hard rubber stopper 65 through which a pair of conventional hard glass tubes 67 and 68 are positioned. Collecting tube 60 which is connected to one end of tube 67 is a flexible tube or transparent or translucent material which enables the user to detect obstructions in the same and view the passage of the fruit fly therethrough. It has an internal surface which is smooth and of such dimension as to readily pass the fruit fly therethrough. The free end of the same has affixed thereto bristles for forming the brush 66 similar to a conventional brush used in the sorting of fruit flies. The tube 68 has a suction tube 70 connected thereto with a mouth piece 75 at the end of the same having an internal diameter sufficient to pass air therethrough in such quantities as to create a suction within the container or vial in which the stopper is positioned. Such a drop in pressure will create a suction at the bursh end of the collecting tube 66 and when specimens are moved by the brush end to a desired segregation area, the user may suck on the end of the mouth piece to draw the specimens through the interior of the collecting tube to the interior of the vial or container in which the stopper is positioned. If desired, a suitable restricting screen (not shown) may be positioned on or associated with the glass tube 68 to prevent movement of flies out of the container. The connection of the flexible collecting tube 67 to the glass tube through the stopper will be a smooth one so that the flies may pass into the culture vial without injury.

The improved system for handling fruit flies removes the danger of ether explosion by substituting carbon dioxide as the anesthetizing medium. This facilitates use of the apparatus by students who can work unsupervised from their instructors. The apparatus is simple to use and the fruit flies are anesthetized before being removed from any container so that there is little chance of flies escaping. The improved transfer device for collecting the flies eliminates the time consuming method of transferring anesthetized flies with the bristles of the conventional camel hair sorting brush. More importantly, the improved system will adapt to any conventional type of culture containers, such as standard vials, and may be used with conventional sorting chambers such as the Petri dish.

Therefore, in considering this invention, it should be remembered that the present disclosure is illustrative only and the scope of the invention should be determined by the appended claims.

I claim:
1. A method of handling Drosophila comprising:
   (a) placing a nozzle connected to a controlled source of carbon dioxide gas over a porous plug in a culture container of Drosophila and allowing a series of controlled pulses of carbon dioxide gas to enter into the culture container through the nozzle and porous plug until all flies therein are anesthetized;
   (b) removing the nozzle and plug from the container and transferring the flies therein into a sorting container;
   (c) sorting the flies in the sorting container into a desired selection;
   (d) withdrawing flies in a desired selection from the sorting container to a new culture container by placing a collecting tube near selected flies in the sorting container and applying a vacuum pulse from the culture container through the collecting tube to transport the flies to the new culture container; and,
   (e) placing a porous plug in the new culture container;
   (f) the porous plug in the culture container being made of a compressible foam material projecting from the end of the culture container with the nozzle having a conically shaped extremity such that carbon dioxide gas is introduced through the porous plug into the culture container by holding the conically shaped extremity of the nozzle against and compressing the porous plug to allow carbon dioxide gas to enter the culture container without escape from the nozzle.

2. The method of handling Drosophila of claim 1 in which the culture container has a vent therein apart from the porous plug to aid in the introduction of carbon dioxide gas into the culture container and permit displacement of air therein through the vent.

3. The method of handling Drosophila of claim 1 and including an additional step of reanesthetizing flies in the sorting container should activity in the flies be noted during sorting by covering the sorting container with a cover having a porous plug therein and introducing carbon dioxide gas into the sorting container.

4. The method of handling Drosophila of claim 1 in which the withdrawing of the flies from the sorting container by a vacuum from the culture container is affected by placing a stopper in the culture container with the collecting tube extending through the stopper and with a suction tube extending also through the stopper such that the user may apply a vacuum from the culture container by applying a vacuum to the suction tube.

5. The method of handling Drosophila of claim 4 in which the sorting of the flies in the sorting container into a desired selection is affected by utilizing the collecting tube with a brush attached thereto to move flies in the sorting container.

6. A method of handling Drosophila comprising:
   (a) placing a nozzle connected to a controlled source of carbon dioxide gas over a porous plug in a culture container of Drosophila and allowing a series of controlled pulses of carbon dioxide gas to enter into the culture container through the nozzle and porous plug until all flies therein are anesthetized;
   (b) removing the nozzle and plug from the container and transferring the flies therein into a sorting container;
   (c) sorting the flies in the sorting container into a desired selection;
   (d) withdrawing flies in a desired selection from the sorting container to a new culture container by placing a collecting tube near selected flies in the sorting container and applying a vacuum pulse from the culture container through the collecting tube to transport the flies to the new culture container;
   (e) placing a porous plug in a new culture container; and,
   (f) including an additional step of reanesthetizing flies in the sorting container should activity of the flies be noted during sorting by covering the sorting container with a cover having a porous plug therein and introducing carbon dioxide gas into the sorting container;
   (g) the porous plugs in the cover of the sorting container and the culture container being compressible foam plugs extending beyond the surface of the containers and in which the nozzle for introducing carbon dioxide gas has a conically shaped extremity to compress the edges of the porous plugs sealing the edges to the nozzle and allowing for passage of the carbon dioxide gas into the containers.

7. The method of handling Drosophila of claim 6 in which the carbon dioxide gas is applied to the culture container by inverting the culture container so that the carbon dioxide gas is applied to the porous plug from beneath the flies therein to prevent the anesthetized flies from contacting the food surface in the base of the culture container.

8. A system for handling Drosophila from a breeding culture through separation and classification to a new breeding culture comprising,
   (a) a first culture vial having an open extremity with a ventilating passage through the wall of the vial and a porous plug positioned in and projecting from the open end of the vial to prevent escape of Drosophila therein;
   (b) a conically shaped nozzle adapted to be connected to an anesthetizing gas and to be positioned over the open end of the porous plug compressing the same and permitting the entrance of the anesthetizing gas into the vial for anesthetizing the Drosophila therein;
   (c) a sorting and classification tray for receiving anesthetized Drosophila with a classification indicia on the base of the same;
   (d) a cover for the sorting and classification tray having vent passages within the same;
   (e) an aperture in the cover of the sorting and classification tray with a porous plug projecting from the top of the same, said porous plug in the cover being adapted to receive the nozzle and introduce anesthetizing gas into the sorting and classification tray when covered; and,
   (f) transferring means for removing anesthetized Drosophila from the sorting and classification tray to a second culture vial including a stopper adapted to be positioned in a second culture vial with a collecting tube having one extremity extending through the stopper to the interior of the second culture vial and with the other extremity having brush means for moving Drosophila on the indicia of the sorting and classification tray, and a suction tube positioned through the stopper and having a mouth piece at the opposite end of the same.

9. The apparatus of claim 8 in which the collector tube is transparent having a smooth interior.

10. The apparatus of claim 8 and including means associated with the suction tube to prevent movement of flies in the vial through the suction tube.

* * * * *

UNITED STATES PATENT AND TRADEMARK OFFICE
CERTIFICATE OF CORRECTION

PATENT NO. : 4,106,438

DATED : August 15, 1978

INVENTOR(S) : Roger K. Nelson

It is certified that error appears in the above—identified patent and that said Letters Patent are hereby corrected as shown below:

Column 1, line 4, "appartus" should be --apparatus--.

Column 4, line 2, "bursh" should be --brush--.

Signed and Sealed this

Sixth Day of February 1979

[SEAL]

Attest:

RUTH C. MASON
Attesting Officer

DONALD W. BANNER
Commissioner of Patents and Trademarks